United States Patent [19]

Bruns et al.

[11] Patent Number: 5,274,134
[45] Date of Patent: Dec. 28, 1993

[54] PROCESS FOR THE STEREOSELECTIVE PREPARATION OF 8α, 12-OXIDO-13, 14,15, 16-TETRANORLABDANE

[75] Inventors: Klaus Bruns, Krefeld; Theo Stalberg, Monheim, both of Fed. Rep. of Germany

[73] Assignees: Henkel Kommanditgesellschaft auf Aktien, Duesseldorf, Fed. Rep. of Germany;

[21] Appl. No.: 768,773
[22] PCT Filed: Apr. 6, 1990
[86] PCT No.: PCT/EP90/00541
§ 371 Date: Oct. 11, 1991
§ 102(e) Date: Oct. 11, 1991
[87] PCT Pub. No.: WO90/12793
PCT Pub. Date: Nov. 1, 1990

[30] Foreign Application Priority Data
Apr. 14, 1989 [DE] Fed. Rep. of Germany ....... 3912318

[51] Int. Cl.⁵ .......................................... C07D 307/92
[52] U.S. Cl. ...................................................... 549/458
[58] Field of Search ......................................... 549/458

[56] References Cited

FOREIGN PATENT DOCUMENTS 61-33184 2/1986 Japan .

OTHER PUBLICATIONS

Aldrich Chemical Company Catalog, Milwaukee, Wis, pp. 55-56(1988).
Ohloff et al., Helvetica Chimica Acta, 68 pp. 2022-2029 (1985).

*Primary Examiner*—Bernard Dentz
*Attorney, Agent, or Firm*—Ernest G. Szoke; Wayne C. Jaeschke; John E. Drach

[57] ABSTRACT

The invention relates to a process for the stereo-selective preparation of 8α,12-oxido-13,14,15,16-tetranorlabdane by dehydration of 8α,12-dihydroxy-13,14,15,16-tetranorlabdane with acid-charged aluminium oxides.

4 Claims, No Drawings

PROCESS FOR THE STEREOSELECTIVE PREPARATION OF 8α, 12-OXIDO-13, 14,15, 16-TETRANORLABDANE

BACKGROUND OF THE INVENTION

This invention relates to a process for the stereoselective preparation of 8α,12-oxido-13,14,15,16-tetranorlabdane and to the use of aluminium oxide having certain properties for the stereoselective preparation of 8α,12-oxido-13,14,15,16-tetranorlabdane.

1. Field of the Invention

8α,12-Oxido-13,14,15,16-tetranorlabdane 2 (Ambroxan ®) is an extremely valuable ambergris fragrance which is found in ambergris, a metabolic secretion of the sperm of whale (Ullmann's Encyklopddie der technischen Chemie, Vol. 20, page 283, Verlag Chemie Weinheim 1981). Ambroxan ® may be synthesized from sclareol by oxidative side chain degradation and subsequent reduction of the lactone formed (sclareolide) in accordance with U.S. Pat. No. 3,050,532. The sclareolide is converted into the odorless diol, 8α,12-dihydroxy-13,14,15,16-tetranorlabdane 1, in known manner, for example by reduction with lithium aluminium hydride (Helv. Chim. Acta 33, 1310 (1950)), with sodium borohydride (Chem. Abstr. 57, 7316a) or with potassium borohydride/lithium chloride mixtures (Chem. Abstr. 94, 15913q).

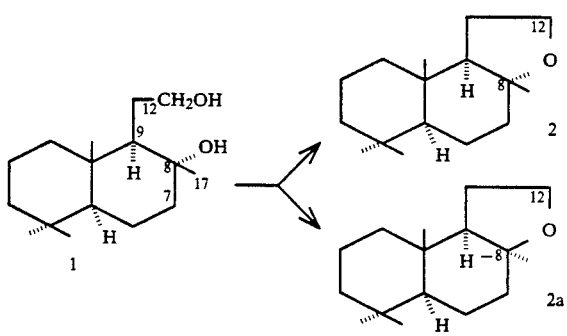

The dehydration of diol 1 with ring closure to Ambroxan ® may be carried out with acidic catalysts, for example p-toluene sulfonic acid, p-sulfonic acid chloride, catalytic quantities of sulfuric acid and also acidic ion exchangers in various solvents, for example toluene, hexane, pyridine, tetrahydrofuran or methanol, preferably at boiling temperature. These processes frequently give mixtures which, in addition to unsaturated alcohols, olefins and the substantially odorless 8-epi-oxide 2a (Helv. Chim. Acta. 68, 2022 (1985)), contain the odor-active, equatorially 8α,12-oxido-linked furan 2, in quantities of only 20 to 50% by weight.

U.S. Pat. No. 3,029,255 describes the use of β-naphthalene sulfonic acid or alumina as dehydration catalysts in the production of Ambroxan ®. In addition to resinification products and olefins, other secondary products are formed in this process, so that the yields of Ambroxan ® are less than 77%.

It is known from JP 61/33184, reported in Chem. Abstr. 105, 134193k (1986), that the theoretical yields of Ambroxan ® can be increased to 85-90.5% by using active white earth, alumina or silica charged with 1 to 20% by weight sulfuric acid, phosphoric acid or polyphosphoric acid. In two Examples, the purity, i.e. the content of odor-active furan 2, is put at 97% and 98%, respectively.

The problem addressed by the present invention was to develop a process for the stereoselective preparation of 8α,12-oxido-13,14,15,16-tetranorlabdane which would enable the yield of Ambroxan ® with a purity of >95% to be increased to considerably more than 90%.

SUMMARY OF THE INVENTION

It has surprisingly been found that Ambroxan ® with a purity of >97% by weight can be obtained in a yield of >95% if 8α,12-dihydroxy-13,14,15,16-tetranorlabdane 1 is dehydrated with aluminium oxides having certain properties.

DESCRIPTION OF THE PREFERRED EMBODIMENTS

Accordingly, the present invention relates to a process for the stereoselective preparation of 8α,12-oxido-13,14,15,16-tetranorlabdane by dehydration of 8α,12-dihydroxy-13,14,15,16-tetranorlabdane 1 with acid-charged aluminium oxides, characterized in that 8α,12-dihydroxy-13,14,15,16-tetranorlabdane 1 is dehydrated with—based on 1—60 to 80% by weight aluminium oxides charged with 0.4 to 0.6% by weight acid and having an apparent density of 0.9 g/cm³ and a particle size range of 0.05 to 0.2 mm (70 to 290 mesh).

The present invention also relates to the use of aluminium oxides charged with 0.4 to 0.6% by weight acid and having an apparent density of 0.9 g/cm³ and a particle size range of 0.05 to 0.2 mm (70 to 290 mesh) for the stereoselective preparation of 8α,12-oxido-13,14,15,16-tetranorlabdane from 8α,12-dihydroxy-13,14,15,16-tetranorlabdane.

The diol 1, which has a water content of 0 to 1.5% by weight, is preferably dehydrated with—based on diol 1—70 to 80% by weight aluminium oxides having the properties mentioned above. Dehydration may be carried out in the absence of solvents, but is preferably carried out in solvents, for example in toluene and/or xylene. The reaction temperature is preferably in the range from 120° to 140° C. The water formed during dehydration may be removed from the reaction mixture, for example by azeotropic distillation. On completion of dehydration, the reaction mixture is worked up in known manner.

EXAMPLE

Preparation of 8α,12-oxido-13,14,15,16-tetranorlabdane (2)

16.5 kg diol 1 dissolved in 22 ml toluene were heated under nitrogen in a water separator until no more water was eliminated. The solution was then cooled to 100° C. and, after the addition of 12.5 kg aluminium oxide (charged with 0.5% by weight hydrochloric acid, apparent density 0.9 g/cm³, particle size range 0.05 to 0.2 mm (70 to 290 mesh)), 1.5 kg water of reaction were azeotropically removed in 6 hours.

The reaction mixture was then filtered through a pressure nutsche. The aluminium oxide filtered off under suction was suspended in 7.5 l toluene and refiltered. The combined organic phases were successively washed twice with 5 liters 1% by weight aqueous nitric acid, twice with 4 liters 1% by weight sodium hydroxide and once with 4 liters 15% by weight aqueous sodium sulfate solution at approximately 45° C. The solvent was then distilled off and the crude product obtained was distilled at 115°–125° C./50 Pa and transferred to a flake-forming roller. 14.5 g (theoretical yield 95%) 8α,12-oxido-13,14,15,16-tetranorlabdane having the following properties were obtained: colorless, crystalline flakes, melting point: 76° to 77° C. (acetonitrile) [77° to 77.5° C. in Helv. Chim. Acta. 68 2022 (1985)] $\alpha_{589}^{25} = -26.7°$ (chloroform; concentration 10.0% by weight). $\alpha_{589}^{20} = -24.7°$ (chloroform; concentration = 1.0% by weight).

What is claimed is:

1. A process for the stereoselective preparation of 8α,12-oxido-13,14,15,16-tetranorlabdane comprising contacting 8α,12-dihydroxy-13,14,15,16-tetranorlabdane comprising contacting 8α,12-dihydroxy-13,14,15,16-tetranorlabdane with from about 60 to about 80% by weight aluminum oxides charged with 0.4 to 0.6% by weight of HCl and having an apparent density of 0.9 g/cm$^3$ and a particle size range of 0.05 to 0.2 mm (70 to 290 mesh).

2. A process as claimed in claim 1, wherein said dihydroxy tetranorlabdane 1 is dehydrated with from about 70 to about 80% by weight of said HCl-charged aluminum oxides by weight of said dihydroxy tetranorlabdane.

3. A process as claimed claim 1 wherein said process is carried out in toluene or xylene.

4. A process as claimed claim 1 wherein said process is carried out at a temperature of from about 120° C. to about 140° C.

* * * * *